(12) United States Patent
Hopkins et al.

(10) Patent No.: US 9,510,740 B2
(45) Date of Patent: *Dec. 6, 2016

(54) AUTO RECOGNITION OF A SHAVER BLADE FOR MEDICAL USE

(75) Inventors: Vernon Hopkins, Worcester, MA (US); Marc R. Amling, Santa Barbara, CA (US); David Chatenever, Santa Barbara, CA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1377 days.

This patent is subject to a terminal disclaimer.

(21) Appl. No.: 12/123,089

(22) Filed: May 19, 2008

(65) Prior Publication Data
US 2008/0211634 A1 Sep. 4, 2008

Related U.S. Application Data

(63) Continuation-in-part of application No. 11/542,461, filed on Oct. 3, 2006, which is a continuation-in-part of application No. 10/095,616, filed on Mar. 12, 2002, now Pat. No. 7,289,139.

(51) Int. Cl.
*A62B 1/04* (2006.01)
*A61B 1/06* (2006.01)
(Continued)

(52) U.S. Cl.
CPC ............. *A61B 1/042* (2013.01); *A61B 1/0002* (2013.01); *A61B 1/00016* (2013.01);
(Continued)

(58) Field of Classification Search
CPC ................... A61B 1/00059; A61B 5/150763; A61B 90/90; A61B 2017/00017; A61B 17/32; A61B 2018/14156
(Continued)

(56) References Cited

U.S. PATENT DOCUMENTS 4,475,540 A 10/1984 Takamatsu et al.
4,478,212 A 10/1984 Asano
(Continued)

FOREIGN PATENT DOCUMENTS

CA 2604858 A1 4/2008
DE 19732442 2/1998
(Continued)

OTHER PUBLICATIONS

Microchip, 1K/2K/4K 1.8V Microwire Serial EEPROM, Microchip Technology Inc., 1996, 12 Pages.
(Continued)

*Primary Examiner* — Tom Y Chang
(74) *Attorney, Agent, or Firm* — Whitmyer IP Group LLC

(57) ABSTRACT

A system for automatically identifying a blade that is connected to a hand piece based on data transmitted from the blade to the hand piece. The blade is provided with a first electronic coupler that communicates with a second electronic coupled positioned in the hand piece such that data related to the blade is transmitted to the hand piece and controllers/computers and in the case of reusable blades, updated data is transmitted to the blade to be saved in a memory coupled to the first electronic coupler. The coupling system can be either a hard wired or wireless coupling between the blade and the hand piece.

19 Claims, 5 Drawing Sheets

(51) Int. Cl.

| | | |
|---|---|---|
| *A61B 1/04* | (2006.01) | |
| *A61B 1/00* | (2006.01) | |
| *G02B 23/24* | (2006.01) | |
| *H04N 5/225* | (2006.01) | |
| *H04N 5/232* | (2006.01) | |
| *A61B 5/15* | (2006.01) | |
| *A61B 17/32* | (2006.01) | |
| *A61B 18/14* | (2006.01) | |
| *A61B 17/00* | (2006.01) | |
| *A61B 17/16* | (2006.01) | |

(52) U.S. Cl.
CPC ...... *A61B 1/00029* (2013.01); *A61B 1/00059* (2013.01); *A61B 17/32002* (2013.01); *A61B 90/90* (2016.02); *A61B 90/98* (2016.02); *G02B 23/2484* (2013.01); *H04N 5/2253* (2013.01); *H04N 5/23203* (2013.01); *H04N 5/23209* (2013.01); *A61B 1/00055* (2013.01); *A61B 1/00062* (2013.01); *A61B 5/150763* (2013.01); *A61B 17/1626* (2013.01); *A61B 17/32* (2013.01); *A61B 2017/00017* (2013.01); *A61B 2017/00199* (2013.01); *A61B 2017/00221* (2013.01); *A61B 2017/00482* (2013.01); *A61B 2018/1415* (2013.01); *A61B 2560/0276* (2013.01); *H04N 2005/2255* (2013.01)

(58) Field of Classification Search
USPC .......................................................... 348/75
See application file for complete search history.

(56) References Cited

U.S. PATENT DOCUMENTS

| | | | |
|---|---|---|---|
| 4,561,429 A | 12/1985 | Sato et al. | |
| 4,777,947 A | 10/1988 | Zwick | |
| 4,996,975 A | 3/1991 | Nakamura | |
| 5,492,527 A | 2/1996 | Glowa et al. | |
| 5,592,727 A | 1/1997 | Glowa et al. | |
| 5,630,180 A | 5/1997 | Kusaka | |
| 5,669,921 A | 9/1997 | Berman et al. | |
| 5,810,858 A | 9/1998 | Berman et al. | |
| 5,830,121 A | 11/1998 | Enomoto et al. | |
| 5,896,166 A | 4/1999 | D'Alfonso et al. | |
| 5,910,776 A | 6/1999 | Black | |
| 5,967,969 A | 10/1999 | Enomoto et al. | |
| 6,001,058 A | 12/1999 | Sano et al. | |
| 6,053,928 A | 4/2000 | Van Wyk et al. | |
| 6,092,722 A | 7/2000 | Heinrichs et al. | |
| 6,141,037 A | 10/2000 | Upton et al. | |
| 6,217,598 B1 | 4/2001 | Berman et al. | |
| 6,295,082 B1 | 9/2001 | Dowdy et al. | |
| 6,313,868 B1 | 11/2001 | D'Alfonso et al. | |
| 6,328,752 B1 | 12/2001 | Sjostrom et al. | |
| 6,364,827 B1 | 4/2002 | Irion et al. | |
| 6,419,684 B1 | 7/2002 | Heisler | |
| 6,436,032 B1 | 8/2002 | Eto et al. | |
| 6,494,827 B1 | 12/2002 | Matsumoto et al. | |
| 6,638,212 B1 | 10/2003 | Oshima | |
| 6,882,868 B1 | 4/2005 | Shattil | |
| 6,968,610 B2* | 11/2005 | Nagao et al. ................... 29/740 |
| 7,237,990 B2 | 7/2007 | Deng | |
| 7,247,161 B2 | 7/2007 | Johnston et al. | |
| 7,273,483 B2* | 9/2007 | Wiener et al. ................ 606/169 |
| 7,289,139 B2* | 10/2007 | Amling et al. ................. 348/65 |
| 7,887,559 B2 | 2/2011 | Deng et al. | |
| 8,588,887 B2 | 11/2013 | Arneson et al. | |
| 2001/0027268 A1 | 10/2001 | Kato | |
| 2001/0052930 A1 | 12/2001 | Adair et al. | |
| 2002/0072736 A1 | 6/2002 | Tierney et al. | |
| 2002/0080248 A1 | 6/2002 | Adair et al. | |
| 2002/0080392 A1 | 6/2002 | Parvulescu et al. | |
| 2002/0120181 A1 | 8/2002 | Irion | |
| 2002/0161385 A1* | 10/2002 | Wiener et al. ................ 606/169 |
| 2003/0065522 A1* | 4/2003 | Wepfer et al. .................... 705/1 |
| 2003/0105478 A1* | 6/2003 | Whitman et al. ............. 606/167 |
| 2003/0145646 A1* | 8/2003 | Henry et al. .................... 73/19.1 |
| 2003/0169333 A1 | 9/2003 | Yazawa et al. | |
| 2003/0174205 A1 | 9/2003 | Amling et al. | |
| 2004/0041031 A1* | 3/2004 | Root et al. ..................... 235/487 |
| 2004/0064019 A1 | 4/2004 | Chang et al. | |
| 2004/0133189 A1 | 7/2004 | Sakurai | |
| 2004/0252188 A1 | 12/2004 | Stantchev et al. | |
| 2004/0267297 A1 | 12/2004 | Malackowski | |
| 2005/0154294 A1 | 7/2005 | Uchiyama et al. | |
| 2005/0187537 A1* | 8/2005 | Loeb et al. ........................ 606/1 |
| 2006/0095096 A1* | 5/2006 | DeBenedictis et al. ........ 607/88 |
| 2006/0149126 A1* | 7/2006 | Ertas et al. .................... 600/101 |
| 2006/0161054 A1* | 7/2006 | Reuss et al. .................. 600/300 |
| 2006/0171693 A1 | 8/2006 | Todd et al. | |
| 2006/0206003 A1 | 9/2006 | Hoeg et al. | |
| 2007/0030345 A1 | 2/2007 | Amling et al. | |
| 2008/0039126 A1* | 2/2008 | Stevens ............. H04L 29/12216 455/500 |
| 2008/0139881 A1 | 6/2008 | Cover et al. | |
| 2008/0177143 A1 | 7/2008 | Yoshida et al. | |
| 2009/0030278 A1 | 1/2009 | Minakuchi | |
| 2010/0004523 A1* | 1/2010 | August et al. ................. 600/365 |
| 2010/0141744 A1 | 6/2010 | Amling et al. | |
| 2013/0133666 A1 | 5/2013 | Swann et al. | |

FOREIGN PATENT DOCUMENTS

| | | |
|---|---|---|
| EP | 0534198 A2 | 3/1993 |
| EP | 1155654 A1 | 11/2001 |
| EP | 1347638 A1 | 9/2003 |
| EP | 1424036 A1 | 6/2004 |
| EP | 1759629 A1 | 3/2007 |
| EP | 1767140 A1 | 3/2007 |
| EP | 1915967 A1 | 4/2008 |
| JP | 59069720 A | 4/1984 |
| JP | S5971020 A | 4/1984 |
| JP | 2001046326 A | 2/2001 |
| JP | 2001078960 A | 3/2001 |
| JP | 2001251611 A | 9/2001 |
| JP | 2001327459 A | 11/2001 |
| JP | 2003325432 A | 11/2003 |
| JP | 2004174008 A | 6/2004 |
| JP | 2006223873 A | 8/2006 |
| JP | 2006254974 A | 9/2006 |
| JP | 2007252843 A | 10/2007 |
| JP | 2007325866 A | 12/2007 |
| JP | 2008501371 A | 1/2008 |
| JP | 2008086777 A | 4/2008 |
| JP | 2008178545 A | 8/2008 |
| JP | 2009517123 A | 4/2009 |
| JP | 2009539544 A | 11/2009 |
| JP | 2010509990 A | 4/2010 |
| WO | 9729678 A2 | 8/1997 |
| WO | 2005039400 A1 | 5/2005 |
| WO | 2005099376 A2 | 10/2005 |
| WO | 2005115106 A2 | 12/2005 |
| WO | 2007061386 A1 | 5/2007 |
| WO | 2007144879 A1 | 12/2007 |
| WO | 2008063565 A2 | 5/2008 |
| WO | 2009027672 A1 | 3/2009 |
| WO | 2009060460 A2 | 5/2009 |

OTHER PUBLICATIONS

European Search Report; Application No. EP 10 17 0427; Sep. 30, 2010; 8 pages.
Extended European Search Report; EP 07 01 9378; Feb. 8, 2008; 4 pages.
International Search Report and Written Opinion of the International Searching Authority; PCT/US09/43733; Jun. 18, 2009; 8 pages.
Medical Connectivity Consulting, "New RFID standard Rubee has health care applications", http://medicalconnectivity.com/2006/09/27/new-rfid-standard-rubee-has-health-care-application, Sep. 27, 2006, 5 Pages.

(56) References Cited

OTHER PUBLICATIONS

European Search Report; Application No. EP 11 17 9304; Issued: Dec. 20, 2011; Mailing Date Jan. 1, 2012; 6 pages.
European Patent Office Communication of a Notice of Opposition Application No. EP10170427.8 Completed: Sep. 24, 2014; Mailing Date: Oct. 1, 2014 6 pages.
Schneider, et al.; "Impacts of Wireless Power on Medical Device Design Safety"; Journal of Medical Devices, Jun. 2009.

\* cited by examiner

AUTO RECOGNITION OF A SHAVER BLADE FOR MEDICAL USE

CROSS-REFERENCE TO RELATED APPLICATIONS

This application is a continuation-in-part application of U.S. patent application Ser. no. 11/542,461 filed Oct. 3, 2006, now U.S. Pat. No. 8,194,122 issued Jun. 5, 2012, which is a continuation-in-part application of U.S. Patent application Ser. No. 10/095,616 filed Mar. 12, 2002, now U.S. Pat. No. 7,289,139 issued Oct. 30, 2007.

FIELD OF THE INVENTION

The invention relates to systems that utilize shaver blades for performing medical procedures and more specifically, to a system and method for automatically identifying and receiving data related to the blade that is connected to a medical device for the purposes of determining blade use and maintenance, inventory tracking and control, and monitoring of various other parameters.

BACKGROUND OF THE INVENTION

Physicians have been utilizing medical devices to perform a variety of medical procedures for many years. Often the devices used include detachable parts or pieces that may wear and need replacement. One such medical device is a shaver or cutting device used by surgeons to perform medical procedures or operations. The type of blade that is used at any one time is selected by the physician or surgeon based upon the type of procedure to be performed.

As used in this application, the terms "blade" or "burr" is used to describe any device used for cutting or shaving, grinding or polishing in a medical procedure, including, for example, a rotating device.

Some blades are disposable (e.g. are provided for one-time use only), while other are designed for multiple uses. In either case, the attached blade is designed to operate within specified design parameters. For example, a blade may be designed to operate up to a maximum speed. The physician would then have to ensure that the hand piece to which the blade is attached is set to operate according to the blade parameters.

With respect to non-disposable blades, it is contemplated that the blade may effectively be used for a certain length of time prior to requiring servicing.

The hand piece, which is grasped by the physician or surgeon during the procedure, is typically provided with controls allowing the surgeon to control the operation of the device. The control may be located directly on the hand piece or at a convenient location adjacent to the physician including a control panel and/or touch screen control.

Blades may come in a variety of sizes for particular applications and surgical procedures and may have operating parameters specific to the blade corresponding to the procedure for which the blade was selected.

As above noted, the hand piece is usually detachable from the blade, and is often conveniently constructed so as to be attachable to a variety of blades having differing cutting properties and specifications. Accordingly, it would be advantageous for the hand piece to be able to identify the blade coupled to the hand piece at any one time. Currently, the settings of the hand piece may be manually adjusted to the blades properties.

It would be advantageous to simplify the task of using the blade and hand piece system by eliminating the need to make manual adjustments to the hand piece in order to optimize the blade settings for an attached blade.

For reusable blades, to ensure optimal blade operation, it would also be advantageous to limit the total amount of use for any particular blade prior to replacement and/or servicing.

Related to the maintenance data are usage characteristics of a blade. For a manufacturer, how its products are used is valuable information. A manufacturer may want to know, for example, how often each product is used, the elapsed time of each use, the maintenance history of the product, and so on. These factors can impact future blade design related to durability, reliability, components and materials used in the manufacturing process.

Therefore, a system is needed that simplifies and optimizes blade and hand piece usage and does not interfere with sensitive electronic equipment such as is found in an operating environment and provides the blade manufacturer with information regarding product usage and maintenance.

SUMMARY OF THE INVENTION

These and other objects are achieved in one embodiment by the provision of a microchip molded or positioned into a detachable blade such as a shaver or burr type blade that couples to a hand piece. The detachable blade may be either disposable or reusable.

The combination blade and hand piece may utilize in one embodiment, Radio frequency identification ("RFID") to wirelessly couple to each other or any other suitable wireless transmission format including, but not limited to infrared. Alternatively, the shaver may utilize a direct connection, such as, for example, a pin connection system to facilitate communication between the blade and the hand piece.

In either case, upon connection of a blade to a hand piece, the hand piece receives data from the blade which may include, for example but is not limited to a serial number of the blade/burr, a minimal speed of the blade, a maximum speed of the blade, run time data (e.g. times used, total run time, etc.), blade type recognition. Based on the received data, the hand piece can then adjust its operational settings. Additionally, data may be written to a memory located on the blade including, for example but not limited to, modified blade use history data.

Accordingly, it is contemplated that the that an electronic coupler or coupling device may be provided on the blade and on the hand piece to electronically couple electronics located on the blade to control circuitry located either in the hand piece or in a controller coupled to the hand piece.

In the wireless format, the electronic couplers variously positioned on the blade and hand piece could comprise first and second transponder/transceivers positioned on the blade and hand piece respectively. The wireless transmission format between the first transponder/transceiver and the second transponder/transceiver could comprise virtually any format, but in one advantageous embodiment may comprise, either an RFID format or a standard called IEEE 1902.1, which is also known as the "RuBee" format. As such, the problems associated with inductive coupling such as radiated EMI and alignment requirements are absent.

Further, the hand piece may be coupled to a controller and/or a computer for control, operation and monitoring of the cutting device. It is contemplated that the controller/computer may be positioned locally for convenient access by the physician. Alternatively, data or information received and/or written to the blade may be saved to a remote computer via a network connection including for example but not limited to, the Internet, an intranet, a Local Area Network (LAN) or a Wide Area Network (WAN).

While the present embodiment has been described in connection with a blade and hand piece combination, there are many additional applications. For example, the present invention may be used in connection with an endoscope read/write apparatus that stores and provides endoscope parameters and endoscope use history data, utilizing a detachable camera capable of accessing the endoscope parameter data and endoscope use history data, and if required, updating and rewriting endoscope use history data to the endoscope for storage. A transponder/transceiver is affixed to the endoscope, and the endoscope transponder/transceiver is capable of transmitting and receiving wireless signals. The endoscope transponder/transceiver is coupled to a memory device that stores electronic representations of the endoscope parameters and endoscope use history data, and when queried, supplies the electronic representations to the endoscope transponder/transceiver. To transmit wireless signals for communication with the endoscope transponder/transceiver, a camera transponder/transceiver is affixed to the camera and set to receive the endoscope transponder/transceiver transmitted wireless signals.

In one advantageous embodiment a system for monitoring a blade coupled to a medical instrument is provided comprising a first electronic coupler affixed to the blade for transmitting and receiving first data and a second electronic coupler affixed to a hand piece for transmitting and receiving second data. The system further comprises a memory device coupled to the first electronic coupler having memory locations for storing data.

In another advantageous embodiment a method for monitoring a blade coupled to a medical instrument is provided comprising the steps of affixing a first electronic coupler to a blade, coupling a memory device to the first electronic coupler and affixing a second electronic coupler to a hand piece. The method further comprises the steps of attaching the blade to the hand piece and transmitting first data from the memory through the first electronic coupler to the second electronic coupler.

In still another advantageous embodiment of the present invention, an endoscope video system is provided for communicating between an endoscope and a detachable camera comprising: a first transponder/transceiver is affixed to the endoscope set to transmit wireless signals containing endoscope parameters and endoscope use history data and set to receive wireless signals containing modified endoscope use history data; a second transponder/transceiver affixed to the detachable camera set to transmit wireless signals containing modified endoscope use history data, and set to receive wireless signals containing the endoscope parameters and endoscope use history data; a memory device coupled to the first transponder/transceiver having memory locations for storing the data contained in the wireless signals; and a camera control unit, coupled to the camera, for receiving and processing the endoscope parameters and endoscope use history data.

In yet another advantageous embodiment of the present invention, an endoscope video system is provided for the transfer of data from an endoscope comprising: a transponder/transceiver affixed to the endoscope, set to transmit wireless signals containing endoscope parameters and endoscope use history data, and set to receive wireless signals containing modified endoscope use history data; and a memory device coupled to the transponder/transceiver having memory locations for storing the data contained in the wireless signals.

In a further advantageous embodiment of the present invention, an endoscope video system is provided for automatically adjusting to the parameters of a plurality of endoscopes, and to provide for the transfer of modified endoscope use history data comprising: a transponder/transceiver positioned on a camera head, set to transmit wireless signals containing modified endoscope use history data, and set to receive wireless signals containing endoscope parameters and endoscope use history data; and a camera control unit, coupled to the camera, for receiving and processing the endoscope parameters and endoscope use history data.

In still a further advantageous embodiment of the present invention, an endoscope video system is provided for communicating between an endoscope and a detachable camera comprising: a first transponder/transceiver attached to the endoscope for transmitting and receiving first data; a second transponder/transceiver attached to the detachable camera for transmitting and receiving second data; and a memory device coupled to the first transponder/transceiver having memory locations for storing data.

The invention and its particular features and advantages will become more apparent from the following detailed description considered with reference to the accompanying drawings.

DETAILED DESCRIPTION OF THE INVENTION

Figure 1:
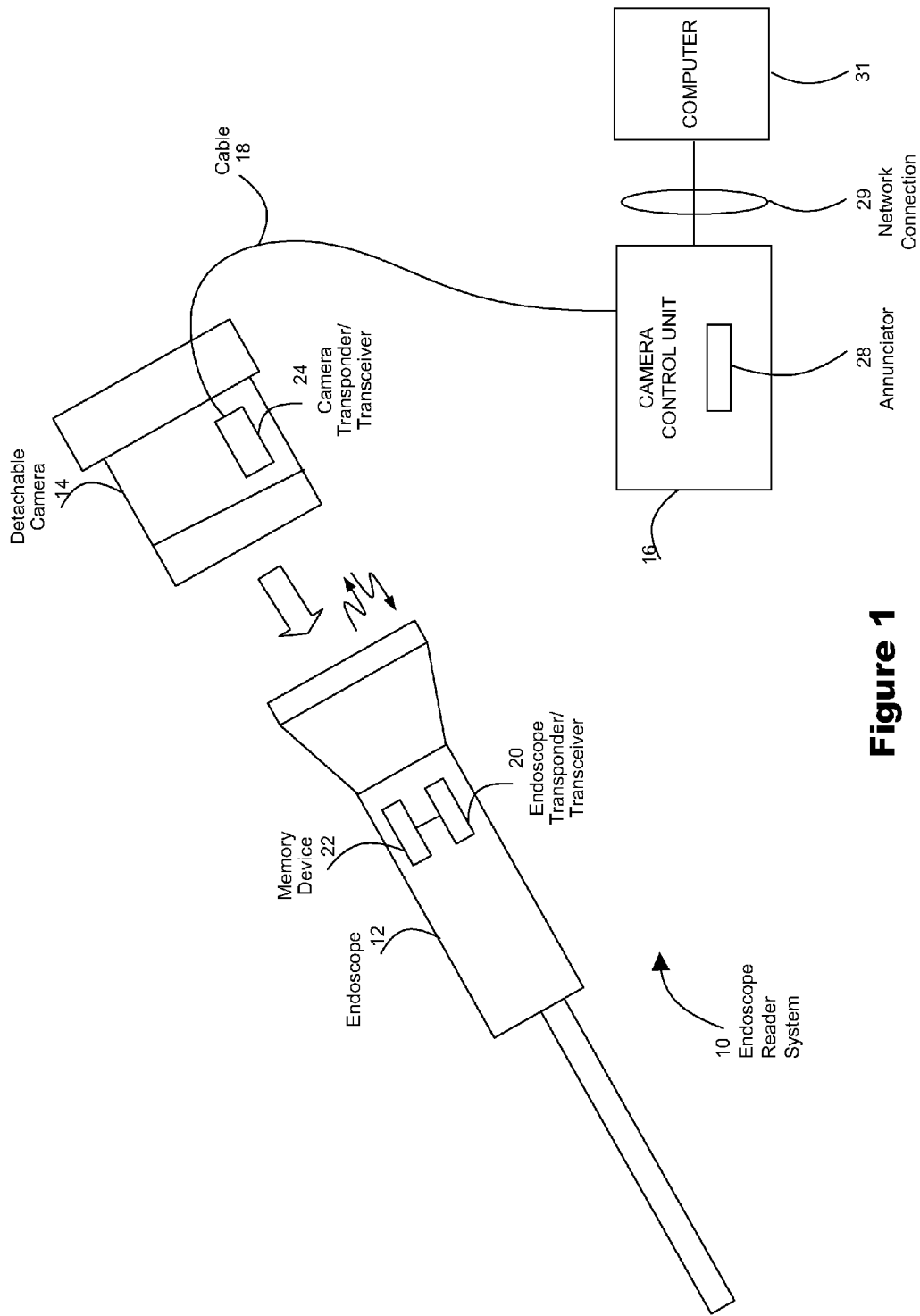
FIG. 1 is an illustration of the assembly of a detachable camera to an endoscope.

Referring now to the drawings, wherein like reference numerals designate corresponding structure throughout the views.

FIG. 1 illustrates an endoscope system 10 for storing and transmitting electronic representations of endoscope characteristics. In accordance with one advantageous embodiment, an endoscope transponder/transceiver 20 is mounted on an endoscope 12 and communicates with a camera head transponder/transceiver 24 mounted on a detachable camera head 14. Endoscope transponder/transceiver 20 and camera head transponder/transceiver 24 may be one of any type of relatively short-range devices well known to those of ordinary skill in the art. Endoscope transponder/transceiver 20 and camera head transponder/transceiver 24 are set so that each is capable of both sending and receiving wireless signals to and from the other.

In one advantageous embodiment, transponder/transceiver 20 and 24 are provided as Radio Frequency (RF) transceivers capable of generating, transmitting and receiving RF signals whether RFID High-Frequency (HF) or Ultra-High Frequency (UHF).

In another advantageous embodiment, transponder/transceiver 20 and 24 may be provided to generate, transmit and receive wireless signals via a standard called IEEE 1902.1, which is also known as the "RuBee" format. Where traditional RFID tags are backscattered transponders, RuBee operates as an active transceiver. RuBee is a bidirectional, on-demand, peer-to-peer, radiating, transceiver protocol operating at wavelengths below 450 KHz. This protocol is advantageous in harsh environments with networks of many thousands of tags and may have an area range of from 10 to about 50 feet.

RuBee offers a real-time, tag-searchable protocol using IPv4 addresses and subnet addresses linked to asset taxonomies that run at speeds of 300 to 9,600 Baud. RuBee Visibility Networks may also be managed by a low-cost Ethernet enabled router. Individual tags and tag data may be viewed as a stand-alone, web server from anywhere in the world. Each RuBee tag, if properly enabled, can be discovered and monitored over the World Wide Web using popular search engines (e.g., Google) or via the Visible Asset's .tag Tag Name Server.

Where a network connection 29 is utilized, it is contemplated that the network may be or include any one or more of, for instance, the Internet, an intranet, a LAN (Local Area Network), a WAN (Wide Area Network) or a MAN (Metropolitan Area Network), a frame relay connection, an Advanced Intelligent Network (AIN) connection, a synchronous optical network (SONET) connection, a digital T1, T3 or E1 line, Digital Data Service (DDS) connection, DSL (Digital Subscriber Line) connection, an Ethernet connection, an ATM (Asynchronous Transfer Mode) connection, FDDI (Fiber Distributed Data Interface) or CDDI (Copper Distributed Data Interface) connections and so forth. In this manner, the camera control unit 16 may be coupled to, for example, a remote computer 31 via the network connection 29 for remote access to the data and/or information transmitted to and from endoscope 12.

Another advantage of RuBee is that it can work well through liquids and metals and consumes less power. From a price perspective, RuBee and traditional RFID are similar in cost.

Endoscope transponder/transceiver 20 is coupled to a memory device 22. Memory device 22 is capable of storing and providing electronic representations of parameters of endoscope 12 to endoscope transponder/transceiver 20. Memory device 22 may be of any type that is programmable by such means as electrically, magnetically, by light frequencies or any type that is commonly known to those of ordinary skill in the art.

As mentioned above, camera head 14 is detachable from endoscope 12 and may be attached to other endoscopes. Camera head 14 is coupled to a camera control unit ("CCU") 16 by cable 18. However, camera head 14 can be coupled to CCU 16 by, for instance; a cable connection, including analog, digital or optical; or a wireless connection. Cable 18 couples CCU 16 to camera head 14 and therefore with camera head transponder/transceiver 24. An annunciator 28 may be incorporated into CCU 16 for the purpose of communicating endoscope parameters to personnel operating the endoscope system 10. Annunciator 28 provides a means by which information concerning the endoscope is communicated to personnel operating the equipment. The annunciator may be a lamp, audible signal, alphanumeric display or other such communication device. Preferably, applicable endoscope parameters received by CCU 16 will subsequently be decoded and displayed on a video monitor for viewing by the endoscope system 10 operator. It is contemplated that memory device 22 may be queried through the present invention by an external computer (not shown) and stored data in memory device 22 retrieved for compilation and analysis. Power for the endoscope mounted circuitry, transponder/transceiver 20 and memory device 22 may be supplied by a power signal from camera head transponder/transceiver 24 derived from a signal from camera head 14, or from an external computer.

Components such as endoscope transponder/transceiver 20, camera head transponder/transceiver 24 and memory device 22, are selected and protected such that they will not be damaged during sterilization of either endoscope 12 or camera head 14. The sterilization may comprise any or all methods of high temperature, chemical or irradiation commonly used in the field. Components employed in endoscope transponder/transceiver 20, memory device 22 and camera head transponder/transceiver 24 must not be degraded by temperatures commonly employed in autoclaves, chemicals such as gluteraldehyde or ethylene oxide, gamma radiation, or any other such sterilization techniques known to those of ordinary skill in the art.

It is also contemplated that various sensors mounted in endoscope 22 will record on memory device 22 peak values that the endoscope 22 is exposed to. This will enable manufacturers and maintenance personnel to determine reasons for endoscope failures and periods for necessary maintenance based upon usage.

It is further contemplated that the endoscope system 10 user will be able to manually "mark" a particular endoscope with a "maintenance required" signal if it is determined by the user that maintenance of the particular endoscope is required. The "marking" can be facilitated by a button or switch locally mounted to the system. Alternatively, the "marking" may take place automatically by the system based upon predetermined criteria. The criteria may include, but is not limited to, elapsed time of use, a certain number of actuations upon receipt of exceeded peak value measurements, or an extended period of time since last maintenance. This "mark" will be transmitted by the endoscope to the CCU and may conspicuously appear on the video screen for future users to see.

The memory device 22 is write-protected such that only factory personnel and/or equipment can remove the "maintenance required" indication. This may be accomplished, for instance, by requiring specific equipment to erase the "maintenance required" indication or by means of a predetermined code that first must be input to enable the removal of the "maintenance required" indication. This will ensure that users of the endoscope system 10 utilize only factory-authorized personnel to repair and maintain the endoscope system 10, which will help to ensure a higher standard of service.

Figure 2:
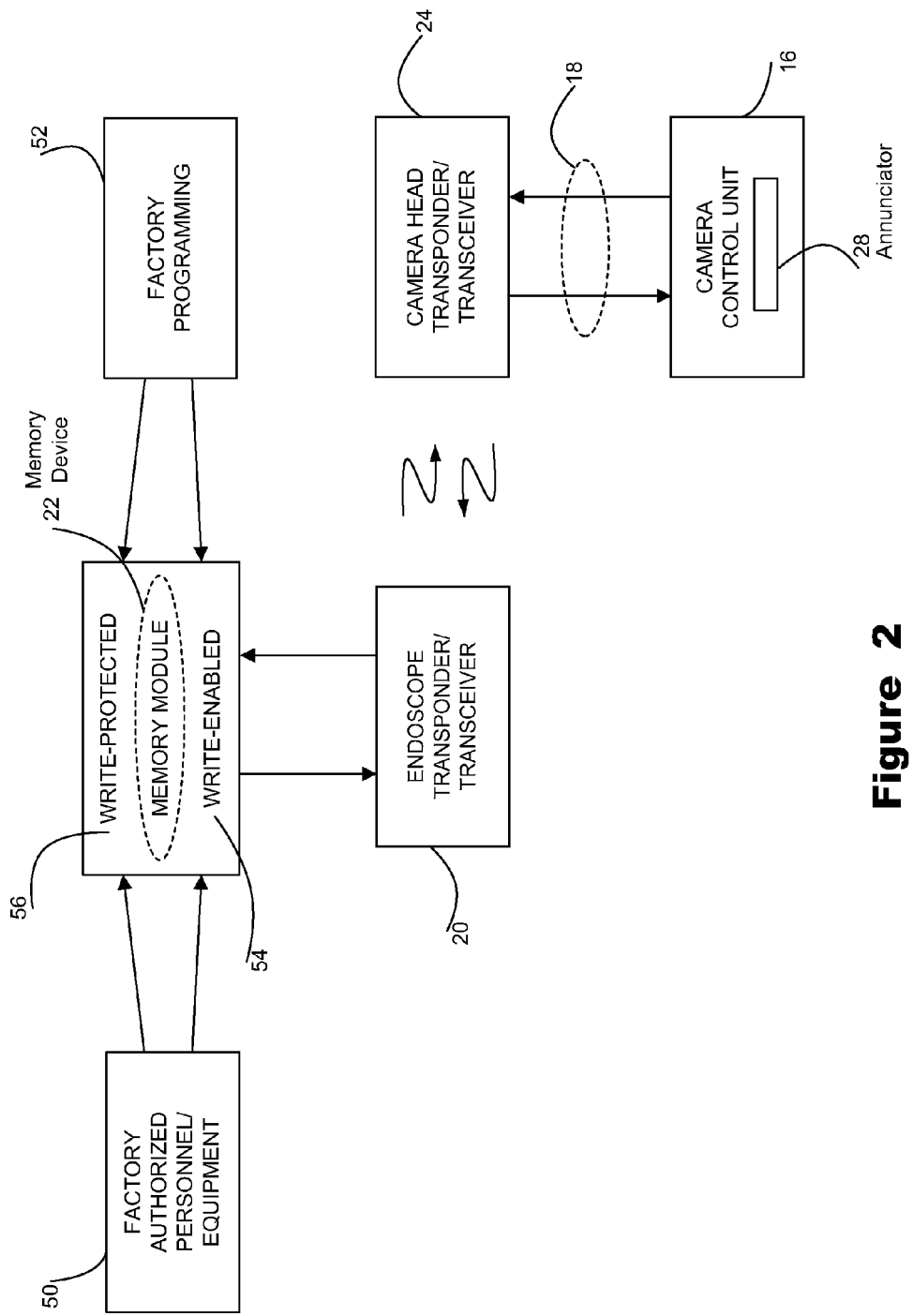
FIG. 2 illustrates the programming of the endoscope memory device and communication with the detachable camera head.

Referring to FIG. 2, memory device 22 stores and supplies electronic representations of endoscope parameters and endoscope use history data. These parameters and data provide a variety of information concerning the endoscope. Information stored in the endoscope would provide all required data for optimal use of the endoscope. In this way, the CCU 16, or other connected medical equipment, would not have to locally or remotely store and access data related to a vast array of different endoscopes. Moreover, as endoscopes are modified and/or improved, corresponding parameters and data are immediately accessible at the time of endoscope use.

The endoscope parameters are broadly classified as fixed or unchanging information. Examples of fixed or unchanging endoscope parameters may include endoscope model and serial number, image relay optics type (e.g., rod lens, fused quartz, fiber optic), endoscope size, optical properties such as a field of view, signal processing data for use by the CCU 16 for video signal optimization, maintenance requirements and interval, settings information for other medical equipment (such as high intensity light sources or insufflators) which are connected and/or controlled by the CCU 16 via a communication bus or any variety of characteristics that may be useful in endoscope, video camera system and other medical equipment usage.

The endoscope use history data is broadly classified as variable or updateable. Examples of variable or updateable endoscope use history data may include, for instance, number of endoscope usages, time of each endoscope use, total time of endoscope operation, number of actuations and medical equipment (used with the endoscope) identification and settings information.

Memory device 22 locations are broadly classified as write-enabled 54 and write-protected 56. Memory device 22 can be capable of disallowing changes to memory locations until specified conditions are met. These conditions may be electrical such as requiring injection of a known signal or series of signals, or programmatic such as a password or any similar such method to prevent unauthorized alteration of the memory device locations. Write-protected locations store parameters that may be altered only during factory programming 52, or by factory authorized personnel/equipment 50. These endoscope parameters are generally, but not necessarily, fixed or unchanging as enumerated above. Write-enabled locations may be altered during factory programming 52, by factory authorized personnel/equipment 50, or with electronic representations of data received from the endoscope transponder/transceiver 20.

Endoscope transponder/transceiver 20 communicates with camera head transponder/transceiver 24 once the camera head transponder/transceiver 24 comes into close proximity. As previously described, power for the endoscope transponder/transceiver 20 is supplied from the camera head transponder/transceiver 24. Transceivers supplied with power in this manner typically have short ranges as compared to similar devices with their own power sources. It is anticipated that the effective range of transmission of the endoscope transponder/transceiver 20 and the camera head transponder/transceiver 24 may advantageously be very short. This is beneficial since an extensive transmission area could disadvantageously result in an endoscope communicating with an unrelated camera head or cause other communication problems with other equipment in the operating room. For example, if the RuBee signal format is utilized, it is contemplated that the signal range will extend from approximately 10 feet to approximately 50 feet.

Camera head transponder/transceiver 24 also exchanges signals with CCU 16 via cable 18. CCU 16 may present the received signals on annunciator 28. For example, data indicating that maintenance of the endoscope is required may be provided by endoscope transponder/transceiver 20 to camera head transponder/transceiver 24 which is forwarded to CCU 16 that, in turn, presents an alert to annunciator 28 that endoscope maintenance is required.

Figure 3:
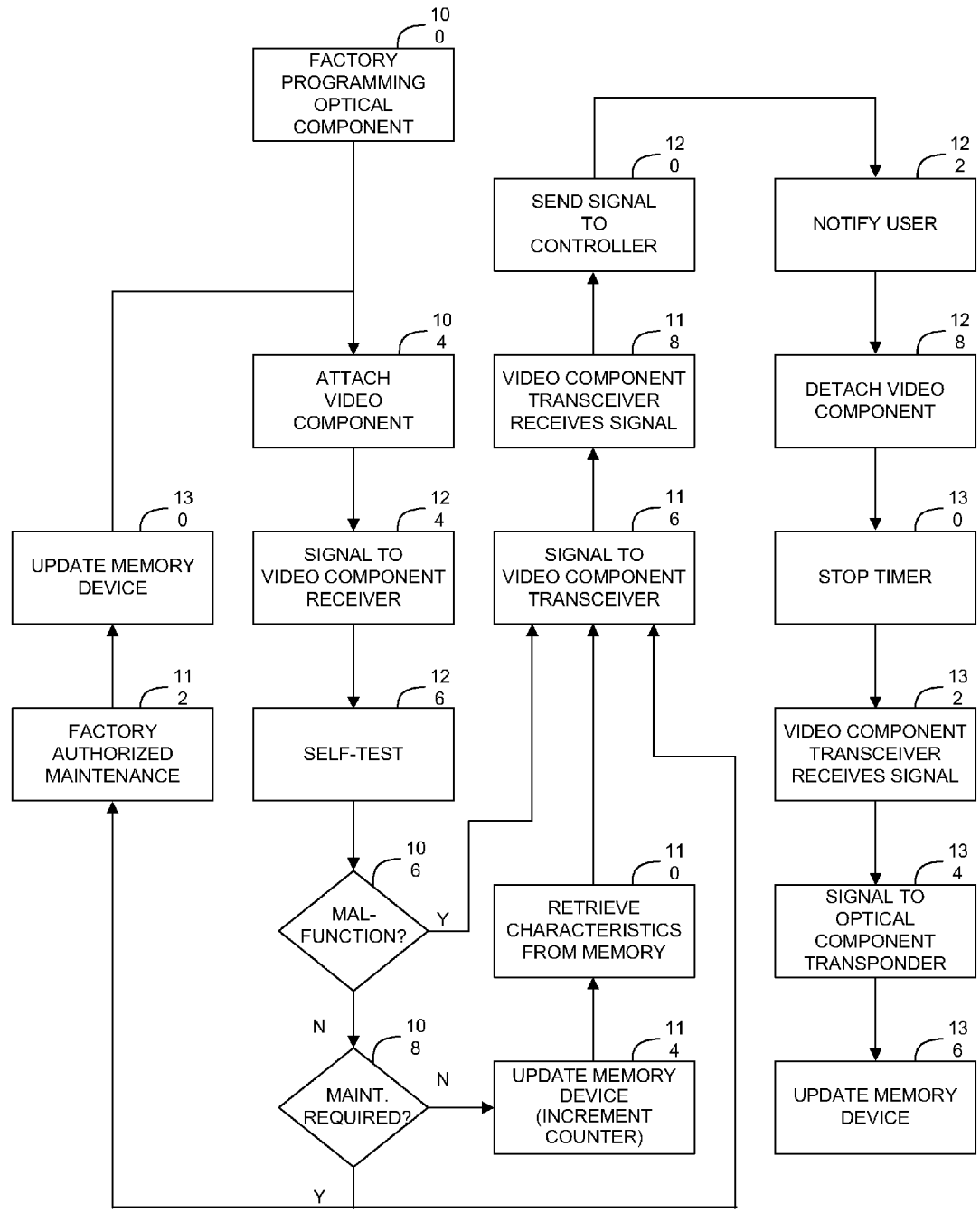
FIG. 3 illustrates a block diagram for implementing the method of the present invention.

FIG. 3 illustrates another application of the present invention. At 100, during manufacture of the endoscope, a memory device mounted in or on the endoscope is programmed with electronic representations of parameters and data specific to that particular endoscope 105. These parameters may include the optical properties, serial number, model number, maintenance schedule, required camera settings, required equipment settings, malfunction codes and other such characteristics and parameters. The memory device will have sufficient additional memory locations to store other data as described below.

Once a camera head is energized, that is, "powered on," a short-range wireless signal is radiated from the camera head transponder/transceiver. Upon the energized camera head being attached to a particular endoscope 110, the wireless signal radiating from the camera head transponder/transceiver powers the endoscope transponder/transceiver. Consequently, the endoscope transponder/transceiver energizes the endoscope memory device, which provides the electronic representation of the endoscope parameters to the endoscope transponder/transceiver with the camera head transponder/transceiver receiving the wireless signal containing the electronic representation of the endoscope parameters from the endoscope transponder/transceiver 115. The CCU, connected to the camera head, decodes the electronic representations of the endoscope parameters and thus "identifies" the endoscope in use. Specific information can then be communicated to the system user 120, such as, but not limited to, endoscope type/model or serial number. The communication may be a visual indicator, an alphanumeric display or printout, an audio signal or any such communication technique. Preferably, the information is displayed on the system video monitor. If the endoscope attached to the camera head does not have a transponder/transceiver and programmed memory device, the video system configuration will remain unchanged.

Once the endoscope is identified and the endoscope parameters are loaded to the CCU, the CCU analysis and increments a "times used" counter (data) 125 for tracking and updating the count of how many times the endoscope was used with an endoscope reader compatible video system. The updated use count data is then written to the endoscope memory device as modified endoscope use history data by means of the camera head transponder/transceiver and the endoscope transponder/transceiver 130.

The amount of time that an endoscope is in use determines the necessity for maintenance, as well as providing statistical data for factory use in design and marketing. Concurrent with the incrementing of the "times used" counter, the CCU also starts an elapsed time ("time in use") clock 135. The elapsed time continues to accumulate as long as the camera head is attached to the endoscope. Periodically, throughout the current use of the endoscope, the CCU, by means of the camera head transponder/transceiver and endoscope transponder/transceiver, updates the endoscope memory device 130 with modified endoscope use history data containing new accumulated "time in use" data 135. In this way, the total "time in use" corresponding to a particular use of the endoscope is stored in the endoscope memory device.

Based upon endoscope parameters extracted from the endoscope memory device, the maintenance status of the endoscope 140 is determined by the CCU. The maintenance requirements criteria, endoscope use history data and any other datum items required for the CCU to determine the current status of the endoscope was previously received by the CCU from the endoscope memory device at 115. If the CCU determines that endoscope maintenance is required 145, the maintenance related information is communicated to the user 150. The communication may be a visual indicator, an alphanumeric display or printout, an audio signal or any such communication technique. Preferably, the information is displayed on the system video monitor.

Depending upon the type of endoscope maintenance required, the user may, be provided the option to continue using the endoscope 160. If the user opts to continue, information pertaining to the continuation is then written to the endoscope memory device by means of the camera head transponder/transceiver and the endoscope transponder/transceiver 130. If the user opts not to continue endoscope use 165 or the continuation option 155 is not provided to the user, it is anticipated that the endoscope will be sent for factory authorized maintenance 170. When the maintenance is completed, the memory device is updated 105 so that the routine maintenance requirements are reset and the video system no longer reports that maintenance is required. The endoscope is again ready for camera head attachment 110 and use.

If endoscope maintenance is not required 175 at 140 or the user opts to continue using the endoscope 160 at 155, the CCU adjusts video processing settings 180 in order to optimize the video system according to endoscope parameters previously retrieved at 115. Additionally, other medical equipment, such as light sources or insufflators settings, may be optimized 180 according to endoscope parameters, as previously described.

Further information gathered, analyzed and compiled may be included in the endoscope use history data by the CCU for storage in the endoscope memory device 130. Endoscope use history data may include data on what camera head, CCU and other medical equipment was used with the endoscope (to include equipment serial numbers, model numbers, software revision numbers, etc.). Any information, which may be useful in determining how well an endoscope functioned, or under what conditions the endoscope functioned, could be included in the endoscope use history data. The endoscope use history data could later be retrieved for demographic or performance analysis purposes. An example is as follows. If a particular endoscope causes numerous CCUs to set exposure levels above a nominal value, this may indicate that the endoscope is not properly relaying images to the camera head. This CCU exposure level data would be included in the endoscope use history data and stored in the endoscope memory device. A review of the stored data would reveal this operational "trend," the endoscope could be inspected and, if necessary, repaired before a catastrophic failure occurs.

As previously described, periodically, the CCU updates the endoscope memory device 130 with modified endoscope use history data containing new accumulated "time in use" data 135. When the camera head is detached from the endoscope 190, the last accumulated "time in use" data will already have been stored in the endoscope memory device. The interval at which the "time in use" data is updated in the endoscope memory device would be frequent enough (i.e., every few minutes or every minute) to ensure the accuracy of the data prior to the camera head being detached from the endoscope.

Figure 4:
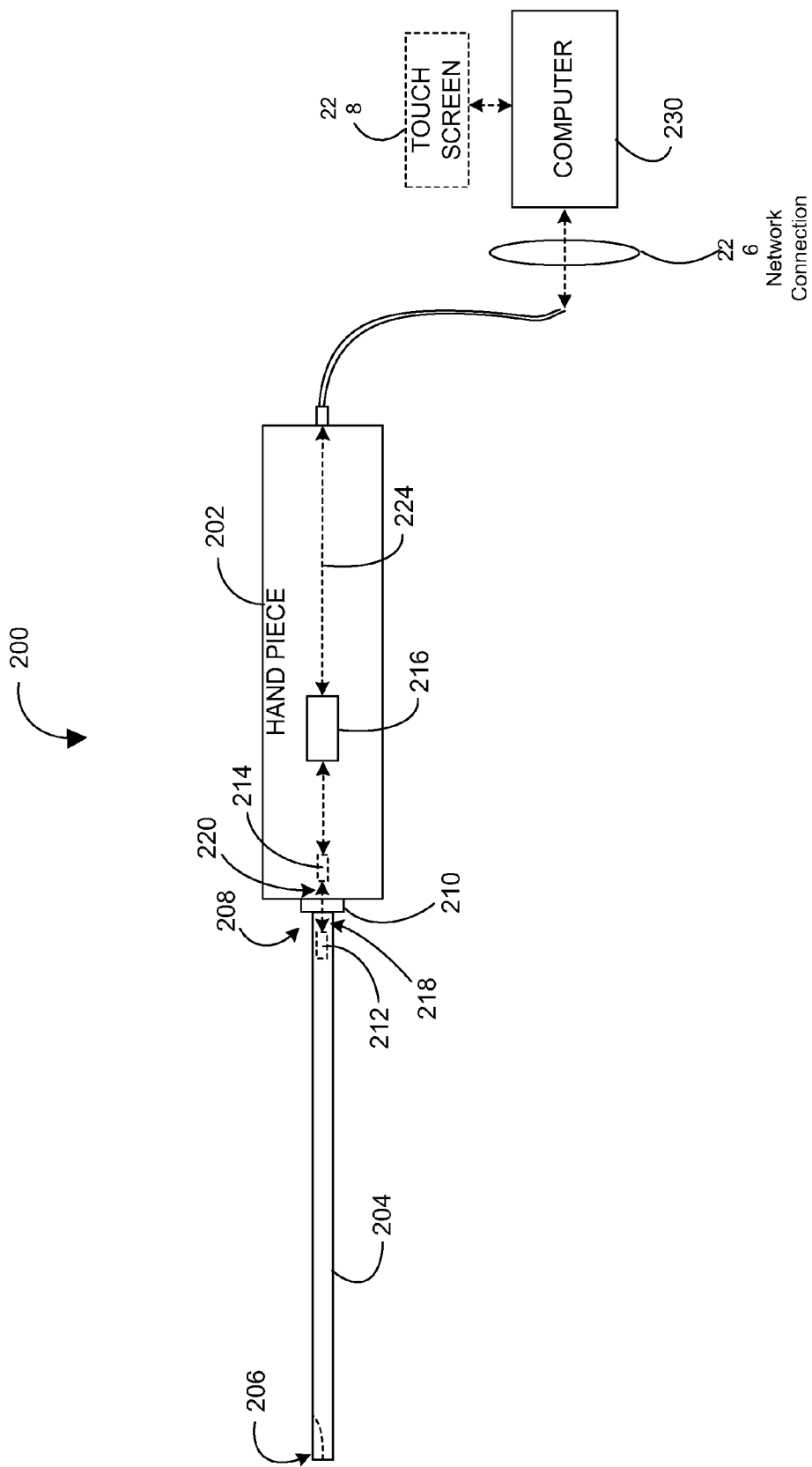
FIG. 4 is an illustration of a blade attached to a hand piece according to an embodiment of the invention.

Referring to FIG. 4 a medical cutting device 200 is illustrated. Medical cutting device 200 generally comprises a hand piece 202 and a blade 204 attachable to the hand piece 202.

In one advantageous embodiment, the blade 204 may be a rotating shaver blade or burr. It is contemplated that virtually any type of rotating shaver blade may effectively be utilized as are commonly know in the art. Additionally, it is further contemplated that blade 204 may comprise either a disposable or a non-disposable blades.

Blade 204 comprises a distal end 206 and a proximal end 208. The rotating cutting portion of blade 204 is positioned at distal end 206. An attachment portion 210 is located at the proximal end 208 for coupling the blade 204 to hand piece 202. It is contemplated that the attachment mechanism for blade 204 may further comprise any appropriate system or method for detachably and securely affixing the blade 204 to the hand piece 202.

Also illustrated in FIG. 4 is a first electronic coupler 212 and a second electronic coupler 214. The first electronic coupler 212 is shown positioned in or on blade 204, while the second electronic coupler 214 is shown positioned in or on hand piece 202.

In one advantageous embodiment, first electronic coupler 212 and second electronic coupler 214 may comprise a wired embodiment including, for example a pin connection to hard wire the electrical connection between the first and second electronic couplers 212, 214. In this embodiment, a first channel 218, which may comprise a number of electrical wires or leads may extend from first electronic coupler 212 to a termination point at attachment portion 210. Additionally, a second channel 220 may also comprise a corresponding number of electrical wires or leads may extend from second electronic coupler 214 to a termination point at the end of hand piece 202 for coupling to the blade 204.

Upon connection, first electronic coupler 212 may transmit data to second electronic coupler 214 (illustrated by the dashed arrow between the couplers 212, 214), which may include, for example, a serial number, operating parameters (e.g. a minimal effective speed and/or a maximum speed) and/or recognition (e.g. blade type) of the blade 204. If the blade is a reusable blade, the data may further include run time data (e.g. times used, total run time, etc.) and maintenance data.

Alternatively, the first and second electronic couplers 212, 214 may comprise a wireless embodiment. In this case, the coupling between the first and second electronic couplers 212, 214 functions similarly to the coupling method as discussed in connection with the endoscope/camera coupling described in connection with FIGS. 1-3 including, for example, RFID and/or RuBee signal formats.

It is further contemplated that either or both first and second electronic couplers 212, 214 may be removable from or integrally molded into blade 204 and/or hand piece 202.

Also provided in hand piece 202 are controls 216, which the physician may use to operate hand piece 202. Controls 216 may comprise local controls the physician uses to control the hand piece 202 as desired and/or may further comprise electronics, which may receive data from first electronic coupler 212. The data received may be used to adjust operation of the hand piece 202 and/or may be transmitted to a remote computer 230 via a line 224 over a network connection 226. Additionally, updated data may be transmitted to first electronic coupler 212 including updated use data.

In another advantageous embodiment, control for the hand piece 202 is provided via a touch screen 228 provided in the sterile operating environment. For example, upon connection of a particular blade 204 to a hand piece 202, data is read from the blade 204 relating to the blade parameters and/or use history, which is fed to computer 230 for display. Operating parameters may be used to adjust the controls for hand piece 202 and use information may be transmitted to the manufacturer.

Figure 5:
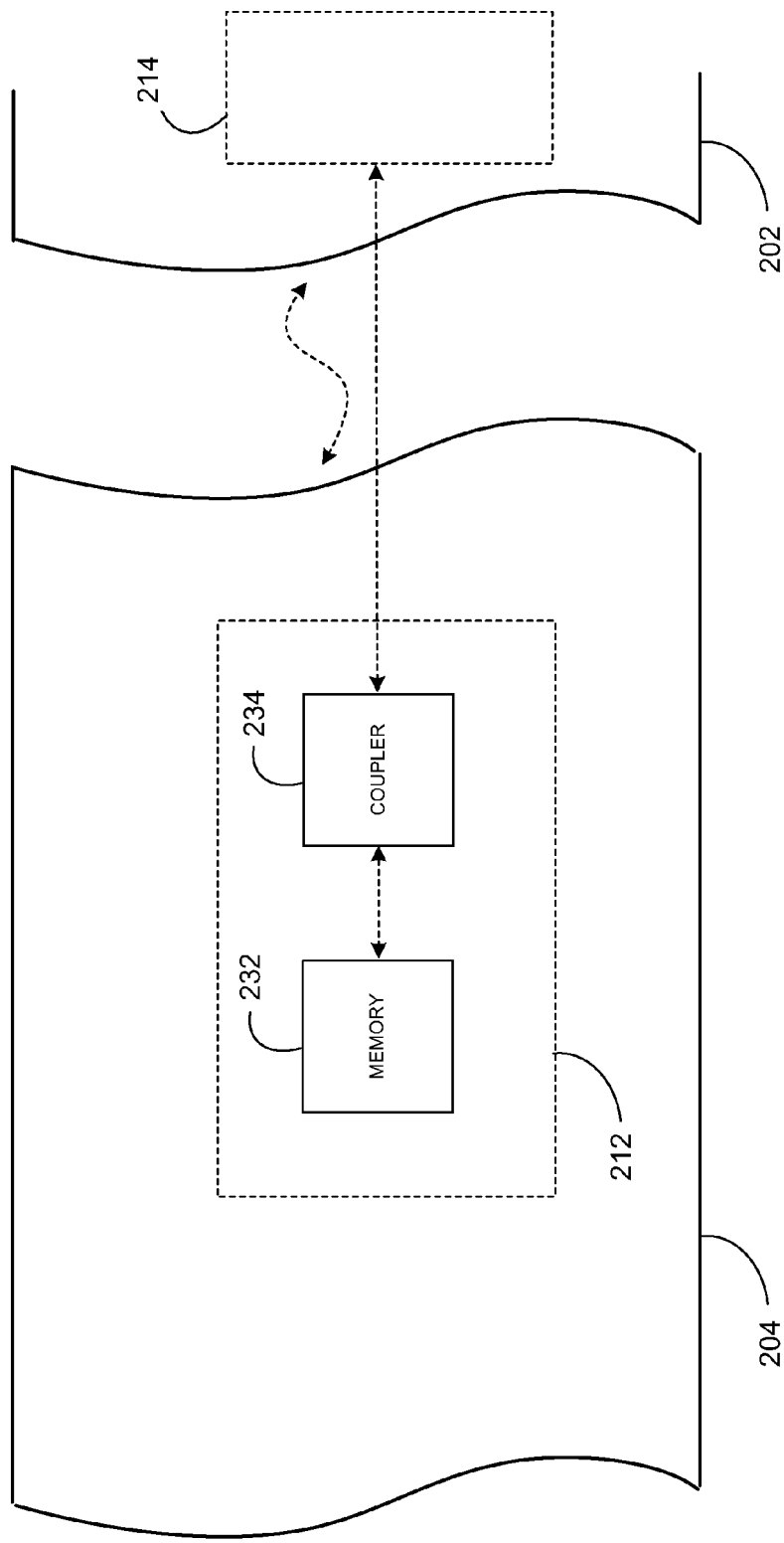
FIG. 5 is a block diagram according to FIG. 4 illustrating the blade and hand piece electronic coupling devices.

Referring now to FIG. 5, first electronic coupler 212 is shown in greater detail including memory 232 and coupler 234. Memory 232 may comprise virtually any type of memory storage device as previously described in connection with FIGS. 1-3. Also illustrated in FIG. 5 are two dashed lines extending from first electronic coupler 212, the first straight line depicting a hard wired configuration and the curved line depicting the wireless configuration as previously described. It is contemplated that first and second electronic couplers 212, 214 may comprise, for example, a microchip set variously positioned to communicate digital information with each other.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for monitoring a medical cutting device comprising:
   a plurality of detachable blades configured to at least one of cut, shave, grind, and polish;
   a hand piece including controls positioned thereon configured to control the operation of one of said plurality of detachable blades attached to said hand piece, each of said plurality of detachable blades being coupleable to said hand piece;
   a plurality of first Radio Frequency (RF) transceivers, wherein each of said plurality of detachable blades has one of said first RF transceivers affixed thereto to transmit blade parameter data and blade use history data;
   a second RF transceiver affixed to said hand piece to receive the blade parameter data, said second RF transceiver coupled to a remote computer via a network; and
   a plurality of memory devices coupled respectively to each of said plurality of first RF transceivers, each of said plurality of memory devices having at least one memory location for storing data;
   wherein said hand piece is configured such that, when one of said plurality of detachable blades is attached to said hand piece, said hand piece automatically adjusts at least one operational setting in accordance with the received blade parameter data so that said hand piece is configured to control the attached blade, and modifies at least one blade use history data value indicating that a detachable blade has been attached to the hand piece, and provides modified blade use history data to the second RF transceiver for transmission to the first RF transceiver and storage in the memory device of the first RF transceiver, wherein the modified at least one blade use history data value is transmitted to the remote computer;
   wherein a wireless transmission format between the first RF transceiver and the second RF transceiver is RuBee format using IPv4 addresses.

2. The system of claim 1, wherein the at least one memory location of each of said plurality of memory devices comprises:
   a write-protected memory location; and
   a write-enabled memory location.

3. The system of claim 1, wherein the blade parameter data comprises blade specification data and maintenance requirements data.

4. The system of claim 1, wherein said plurality of detachable blades are at least one of disposable and non-disposable.

5. The system of claim 1, wherein said plurality of memory devices are positioned in or on said plurality of detachable blades respectively.

6. The system of claim 1, wherein at least one of said plurality of detachable blades comprises a rotating shaver blade.

7. The system of claim 1, wherein the network is selected from the group consisting of: the Internet, an intranet, a LAN, a WAN, a MAN and combinations thereof.

8. The system of claim 1, wherein a marking signal is automatically generated when the system determines that maintenance of either the attached blade or said hand piece, or both, is required.

9. The system of claim 8, further comprising an input device allowing a user to manually generate the marking signal.

10. The system of claim 1, wherein the at least one blade use history data is selected from the group consisting of: how often the blade is used, the elapsed time of each use, the maintenance history of the blade, and combinations thereof.

11. The system of claim 1, wherein the blade parameter data is selected from the group consisting of: a minimal speed of the blade, a maximum speed of the blade, and combinations thereof.

12. The system of claim 3, wherein the blade specification data is selected from the group consisting of: a serial number, blade type, and combinations thereof.

13. The system of claim 1, wherein tag-searchable data is stored in each of said plurality of memory devices;
   wherein the network is the Internet; and
   wherein the tag-searchable data can be discovered and monitored over the World Wide Web.

14. The system of claim 1, wherein wireless transmission between the first RF transceiver and the second RF transceiver is substantially unattenuated by liquids and metals.

15. The system of claim 1, wherein each of the plurality of first RF transceivers and the second RF transceiver generate, transmit, and receive wireless transmissions via a low frequency carrier.

16. The system of claim 15, wherein the low frequency carrier has at least one operating frequency at or below 450 MHz.

17. The system of claim 1, wherein each of the plurality of first RF transceivers and the second RF transceiver is an active transceiver.

18. The system of claim 1, wherein each of the plurality of first RF transceivers and the second RF transceiver generate, transmit, and receive wireless transmissions in the form of longwave magnetic signals.

19. The system of claim 1, wherein wireless transmissions between the first RF transceiver and the second RF transceiver have a baud rate between 300 and 9,600 Baud.

* * * * *